United States Patent
Pietrantonio

(10) Patent No.: US 8,925,118 B2
(45) Date of Patent: *Jan. 6, 2015

(54) CONCUSSION INDICATOR

(71) Applicant: Antonio Pietrantonio, Seabrook, NH (US)

(72) Inventor: Antonio Pietrantonio, Seabrook, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/094,885

(22) Filed: Dec. 3, 2013

(65) Prior Publication Data

US 2014/0288462 A1    Sep. 25, 2014

Related U.S. Application Data

(63) Continuation of application No. 13/847,661, filed on Mar. 20, 2013, now Pat. No. 8,621,673.

(51) Int. Cl.
| | | |
|---|---|---|
| *A42B 3/06* | (2006.01) | |
| *A42B 3/04* | (2006.01) | |
| *A61B 5/00* | (2006.01) | |
| *A42B 3/00* | (2006.01) | |

(52) U.S. Cl.
CPC .............. *A42B 3/0453* (2013.01); *A61B 5/4076* (2013.01); *A61B 5/6803* (2013.01); *A61B 5/742* (2013.01)
USPC ................ 2/425; 2/410; 2/411; 2/412; 2/413; 2/414

(58) Field of Classification Search
CPC ....... G01P 15/036; G01P 15/06; G01P 15/04; G01P 15/03; G01P 1/127; G01P 15/0891; G01P 15/135; G01P 15/00; G01P 15/0922; G01P 15/122; G01P 15/038; G01L 5/0052; A42B 3/046; A42B 3/063; A42B 3/12; A42B 3/066; A42B 3/068; A42B 3/069; A42B 3/121; A63B 71/10; A63B 2220/53; A63B 2220/40; A63B 2230/00; A63B 2243/0045; A63B 2243/0066; A63B 2243/007; A63B 69/004; A63B 71/081
See application file for complete search history.

(56) References Cited

U.S. PATENT DOCUMENTS

| | | | | |
|---|---|---|---|---|
| 2,250,275 | A * | 7/1941 | Riddell | 2/424 |
| 2,475,728 | A * | 7/1949 | Smith | 200/61.45 R |
| 2,601,440 | A * | 6/1952 | Kerrigan | 116/203 |
| 2,825,297 | A * | 3/1958 | Harrison | 116/203 |
| 2,976,732 | A * | 3/1961 | Hautly | 73/492 |
| 3,021,813 | A * | 2/1962 | Rips | 116/201 |
| 3,312,188 | A * | 4/1967 | Lode et al. | 116/203 |
| 3,369,521 | A * | 2/1968 | Meeder, Jr. | 116/203 |
| 3,373,716 | A * | 3/1968 | Williams | 116/203 |

(Continued)

*Primary Examiner* — Bobby Muromoto, Jr.
(74) *Attorney, Agent, or Firm* — Lambert & Associates; Gary E. Lambert; David J. Connaughton, Jr.

(57) ABSTRACT

A concussion indicator that may easily be applied to a helmet is provided. The concussion indicator may visually or audibly provide indicators relating to impacts creating accelerations of the helmet that likely cause a concussion. In some embodiments, three separate indicators may be used within a single base; each indicator is configured to indicate at impacts relating to different concussion grades. A rear of the base is attachable to a surface such as an interior or exterior of a helmet. Upon a concussion triggering acceleration, the concussion indicator will indicate that a concussion is likely. This display may be seen or heard by observers if the indicator is on an exterior of the helmet, and by the user or someone who removes the user's helmet if it is on the inside of the helmet.

20 Claims, 2 Drawing Sheets

(56) References Cited

U.S. PATENT DOCUMENTS

| | | | | |
|---|---|---|---|---|
| 3,413,951 A | * | 12/1968 | Schorn et al. | 116/267 |
| 3,461,730 A | * | 8/1969 | Peters | 73/514.09 |
| 3,515,091 A | * | 6/1970 | Smith | 116/203 |
| 3,616,463 A | * | 11/1971 | Theodore et al. | 2/412 |
| 3,623,449 A | * | 11/1971 | Knutson | 116/203 |
| 3,688,734 A | * | 9/1972 | Davis et al. | 116/215 |
| 3,707,722 A | * | 12/1972 | Itoh | 346/7 |
| 3,782,204 A | * | 1/1974 | Boardman | 73/492 |
| 3,835,809 A | * | 9/1974 | Sinn, Jr. | 116/203 |
| 3,866,909 A | * | 2/1975 | DeSantis | 482/88 |
| 3,909,568 A | * | 9/1975 | Greenhut | 200/61.45 R |
| 3,921,463 A | * | 11/1975 | Robbins | 73/492 |
| 3,946,441 A | * | 3/1976 | Johnson | 2/412 |
| 4,060,004 A | * | 11/1977 | Scholz et al. | 340/436 |
| 4,064,565 A | * | 12/1977 | Griffiths | 2/412 |
| 4,068,613 A | * | 1/1978 | Rubey | 116/203 |
| 4,125,085 A | * | 11/1978 | Rubey | 116/203 |
| 4,177,751 A | * | 12/1979 | Rubey | 116/201 |
| 4,237,736 A | * | 12/1980 | Wright | 73/492 |
| 4,361,106 A | * | 11/1982 | Eklof | 116/203 |
| 4,470,302 A | * | 9/1984 | Carte | 73/492 |
| 4,663,785 A | * | 5/1987 | Comparetto | 2/413 |
| 4,688,244 A | * | 8/1987 | Hannon et al. | 340/426.28 |
| 4,763,275 A | * | 8/1988 | Carlin | 702/41 |
| 4,937,888 A | * | 7/1990 | Straus | 2/411 |
| 4,982,684 A | * | 1/1991 | Rubey | 116/203 |
| 5,027,105 A | * | 6/1991 | Dailey et al. | 340/571 |
| 5,242,830 A | * | 9/1993 | Argy et al. | 436/5 |
| 5,269,252 A | * | 12/1993 | Nagai | 116/203 |
| 5,343,569 A | * | 9/1994 | Asare et al. | 2/412 |
| 5,546,609 A | * | 8/1996 | Rush, III | 2/413 |
| 5,621,922 A | * | 4/1997 | Rush, III | 2/422 |
| 6,065,158 A | * | 5/2000 | Rush, III | 2/412 |
| 6,070,271 A | * | 6/2000 | Williams | 2/412 |
| 6,301,718 B1 | * | 10/2001 | Rigal | 2/411 |
| 6,332,226 B1 | * | 12/2001 | Rush, III | 2/412 |
| 6,551,834 B2 | * | 4/2003 | Carpenter et al. | 436/86 |
| 6,848,389 B1 | * | 2/2005 | Elsasser et al. | 116/203 |
| 6,854,133 B2 | * | 2/2005 | Lee et al. | 2/421 |
| 7,328,462 B1 | * | 2/2008 | Straus | 2/411 |
| 7,509,835 B2 | * | 3/2009 | Beck | 73/12.01 |
| 7,526,389 B2 | * | 4/2009 | Greenwald et al. | 702/55 |
| 7,743,640 B2 | * | 6/2010 | Lampe et al. | 73/12.04 |
| 7,918,179 B2 | * | 4/2011 | Pan et al. | 116/203 |
| 8,056,391 B2 | * | 11/2011 | Petelenz et al. | 73/11.01 |
| 8,074,489 B2 | * | 12/2011 | Ishikawa et al. | 73/12.04 |
| 8,191,421 B2 | * | 6/2012 | Petelenz et al. | 73/579 |
| 8,234,994 B1 | * | 8/2012 | Branch | 116/203 |
| 8,240,270 B2 | * | 8/2012 | Naruishi | 116/203 |
| 8,387,552 B2 | * | 3/2013 | Branch | 116/203 |
| 8,397,551 B2 | * | 3/2013 | King et al. | 73/35.14 |
| 8,621,673 B1 | * | 1/2014 | Pietrantonio | 2/425 |
| 2004/0025231 A1 | * | 2/2004 | Ide et al. | 2/425 |
| 2004/0074283 A1 | * | 4/2004 | Withnall et al. | 73/12.12 |
| 2005/0039669 A1 | * | 2/2005 | Elsasser et al. | 116/203 |
| 2005/0217558 A1 | * | 10/2005 | Fitzer et al. | 116/203 |
| 2005/0278835 A1 | * | 12/2005 | Ide et al. | 2/424 |
| 2006/0137073 A1 | * | 6/2006 | Crisco | 2/142 |
| 2007/0089480 A1 | * | 4/2007 | Beck | 73/12.01 |
| 2007/0194943 A1 | * | 8/2007 | Fitzer et al. | 340/686.1 |
| 2007/0245810 A1 | * | 10/2007 | Carter et al. | 73/53.01 |
| 2008/0208073 A1 | * | 8/2008 | Causevic | 600/544 |
| 2009/0249858 A1 | * | 10/2009 | Ishikawa et al. | 73/12.06 |
| 2010/0180457 A1 | * | 7/2010 | Katoh et al. | 33/366.11 |
| 2010/0275676 A1 | * | 11/2010 | King et al. | 73/35.14 |
| 2011/0287553 A1 | * | 11/2011 | Hassan et al. | 436/164 |
| 2012/0210498 A1 | | 8/2012 | Mack | |

\* cited by examiner

CONCUSSION INDICATOR

PRIORITY CLAIM

This application is a continuation of, and claims priority from U.S. Non-Provisional patent application Ser. No. 13/847,661, filed on Mar. 20, 2013.

BACKGROUND OF THE INVENTION

1. Field of the Invention

The present invention relates generally to concussion indicating devices. More particularly the present invention relates to a device that may attach to a helmet and indicate three different levels of concussion severity.

2. Description of Related Art

There are many situations in which a helmet, hard-hat, or other protective headgear is essential for user safety. For example, many jobs are performed in hazardous areas requiring a hard hat for protection. For example, jobs include building or road construction, manufacturing involving hazardous machinery or materials, logging, and many others.

The challenge of preventing head injuries also extends to athletics. Participation in athletic activities is increasing at all age levels. All participants may be potentially exposed to physical harm as a result of such participation. Physical harm to the head is more likely to occur in athletic events where collisions between participants frequently occur (e.g., football, field hockey, lacrosse, ice hockey, and the like). Approximately 300,000 athletes incur concussions in the United States each year. This may be a conservative estimate because many minor head injuries and low grade concussions go unreported. Although most concussions occur in high-impact sports, athletes in low-impact sports are not immune to mild traumatic brain injury.

Head injuries are caused by positive and negative acceleration forces experienced by the brain and may result from linear or rotational accelerations (or both). Both linear and rotational accelerations are likely to be encountered by the head at impact, damaging neural and vascular elements of the brain.

At the school level, school authorities have become sensitive to the risk of injury to which student participants are exposed, as well as to the liability of the school system when injury results. Greater emphasis is being placed on proper training and instruction to limit potential injuries. Some players engage in reckless behavior on the athletic field or do not appreciate the dangers to which they and others are subject by certain types of impacts experienced in these athletic endeavors. Unfortunately, the use of mouth guards and helmets does not prevent all injuries. One particularly troublesome problem is when a student athlete experiences a head injury, such as a concussion, of undetermined severity even when wearing protective headgear. Physicians, trainers, and coaches utilize standard neurological examinations and cognitive questioning to determine the relative severity of the impact and its effect on the athlete. Return to play decisions can be strongly influenced by parents and coaches who want a star player back on the field.

The same problem arises in professional sports where the stakes are much higher for a team, where such a team loses a valuable player due to the possibility of a severe head injury. Recent medical data suggests that lateral and rotational forces applied to the head and neck area (for example, flexion/extension, lateral flexion, and axial rotation) are more responsible for axonal nerve damage than previously thought. Previous medical research had indicated that axially directed forces (such as spinal compression forces) were primarily responsible for such injuries.

Identifying the rate of acceleration that causes brain injury may assist in prevention, diagnosis, and return-to-play decisions. Most field measurements assess the acceleration or deceleration (hereinafter referred to collectively as accelerations) experienced by the player with accelerometers attached to the helmet. These devices test the impact to the skull of a player. If an athlete suffers a concussion, for example, it will be possible to determine if the relative magnitude of an impact is dangerously high relative to a threshold to which each sensing device is adjusted, taking into consideration the size and weight of the player.

Another attempt performs testing impact acceleration to the head with an intraoral device which provides acceleration information of the brain in various sports. Other attempts have been made, however all these attempts can be costly to implement and fail to provide full information to professionals in real-time.

Therefore, what is needed is a simple, low-cost device that may effectively measure a likelihood of concussion upon a given impact, and what grade that concussion may be.

SUMMARY OF THE INVENTION

The subject matter of this application may involve, in some cases, interrelated products, alternative solutions to a particular problem, and/or a plurality of different uses of a single system or article.

In one aspect, a concussion indicator for attaching to a helmet is provided. A base defines a first, second, and third chamber, with an impact capsule disposed within each chamber. Each impact capsule is viewable by an observer and is configured to provide a visual indication upon receiving an acceleration of predetermined rate. An adhesive is disposed on a rear of the base, allowing the base to be attached to a surface of the helmet. The indicator may be attachable to an inside or outside of a helmet.

Non-limiting examples of helmets with which the concussion indicator may be used may include sports helmets such as baseball, football, hockey or lacrosse, recreational helmets such as boating, skiing, motorcycle or bicycle helmets, construction helmets (hard hats) and the like.

DETAILED DESCRIPTION

Figure 3:
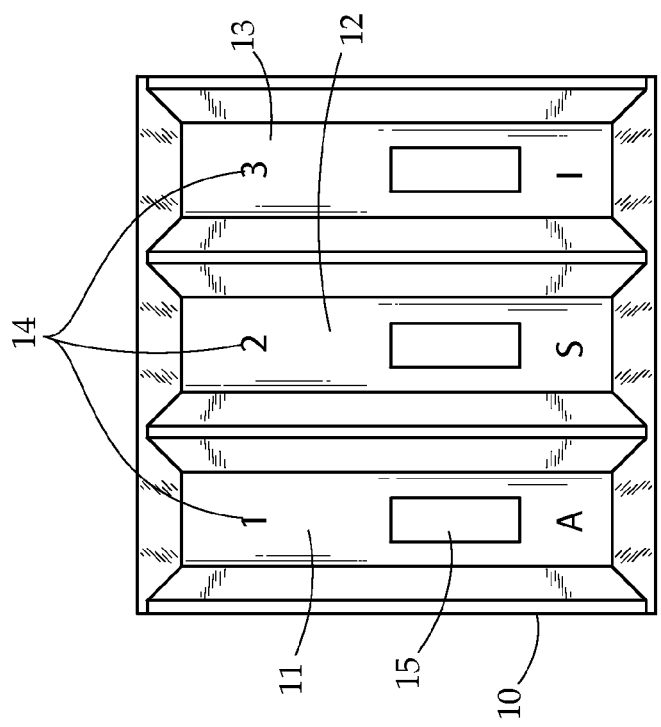
FIG. 3 provides a rear view of an embodiment of the concussion indicator

The detailed description set forth below in connection with the appended drawings is intended as a description of presently preferred embodiments of the invention and does not represent the only forms in which the present invention may be constructed and/or utilized. The description sets forth the functions and the sequence of steps for constructing and operating the invention in connection with the illustrated embodiments.

Generally, the present invention concerns a concussion indicator that may easily be applied to a helmet of a user. The concussion indicator may provide an indication or indications relating to impacts that likely cause a concussion. In one embodiment, three separate indications may be provided from three separate indicating devices, each indicating device configured to indicate at impacts relating to different concussion grades. In another embodiment, a single indicator may provide multiple indications for different concussion levels.

The concussion indicator is formed from a base which provides its structure and stores its components. Within the base is an impact capsule or similar indicating device configured to visually or audibly provide an indication in the event that it experiences an acceleration of a pre-determined rate. A rear of the base is attachable to a surface such as an interior or exterior of a helmet. As such, the concussion indicator base may be connected to a helmet of a user. Upon a concussion triggering acceleration, the concussion indicator will display that a concussion is likely. This display may be seen or heard by observers if the indicator is on an exterior of the helmet, and by at least the user or someone who removes the user's helmet if it is on the inside of the helmet.

The base may be formed of any material capable of being attached to a helmet and capable of holding the indicating device(s). For example, materials of which the base may be made include, but are not limited to: plastics, composite materials, wood, metals, and the like. In some embodiments, the base may be flexible to allow it to attach to a contoured surface of a helmet.

In one embodiment, the base may be substantially rectangular in shape. The base may define three chambers, each chamber separated from the other by a wall. An impact capsule, as discussed further below, may be positioned within each of the three chambers. The three impact capsules may be configured to trigger at different levels of impact, one at a grade one concussion impact, one at a grade two concussion impact, and the final one at a grade three concussion impact. The base may further define an opening or window into each chamber. Through the window, the impact capsule may be visible. As such, an observer may indicate a change in the impact capsule through the window of the base. Based on this, the observer would be able to determine if a concussion is likely, and if so, what grade of concussion.

In a further embodiment, each of the three chambers may have indented regions between them defined by the base. These indented regions may aid in flexibility, and may provide easier distinction between the chambers, among other things. In another embodiment, each chamber may be marked with a different number: 1 through 3 to indicate concussion grade indication.

The rear surface of the base may be attachable to a helmet in any manner. In one embodiment, the rear surface may comprise a quantity of adhesive; this adhesive may be used to adhere the base to a helmet surface. In another embodiment, the rear of the base and the helmet may connect by a hook and loop fastener system. In still another embodiment, the rear of the base may be clipped into the helmet.

In a particular embodiment, the base may be substantially rectangular in shape. In a further embodiment, the base may be a one inch by one inch square, with a quarter inch height.

In one embodiment, the indicating device may be an impact capsule. The impact capsule may be any structure capable of being stored by the base that can provide a visual indication that an acceleration of a particular rate has been received by the capsule. In one embodiment, the impact capsule may be formed as a capsule having a membrane divider and two chemicals within the capsule separated by the membrane. Upon an impact causing a high enough acceleration, the membrane is designed to rupture. Once ruptured, a chemical reaction may occur or a colored dye may be released, providing a visual indication such as a color change. These membrane divider impact capsules preferably have transparent or translucent walls, or a window allowing an observer to see the color change within the capsule. In embodiments utilizing multiple impact capsules, the membrane within each impact capsule may be configured to rupture under different acceleration rates, thereby indicating different likely concussion grades. These impact capsules may operate regardless of orientation, and may register an impact in any direction. Therefore, location of the concussion indicator on the helmet is not imperative, thus allowing the concussion indicator to be installed by a user without any training.

In a further embodiment, different impact capsules configured to show different levels of impact may have indicative colors. For example, an impact capsule configured to indicate at a grade 1 concussion may provide a yellow colored indication, a grade 2 concussion may indicate orange, and a grade 3 concussion may indicate red.

Concussion grades may vary and can be determined in different manners. As such, the impact capsules may be configured to identify concussions at different acceleration rates in different embodiments. The concussion grading may be based on different guidelines such as the Cantu guidelines, the Colorado Medical Society guidelines, or the American Academy of Neurology guidelines. In a particular embodiment, an indicator capsule configured to indicate a grade 1 concussion may trigger upon receiving an impact causing a 50 g acceleration an indicator for a grade 2 concussion may trigger at 70 g, and an indicator for a grade 3 concussion may trigger at 90 g.

In a further embodiment, the chambers and/or impact capsules may be crush resistant. As such, the concussion indicator will be operative even under a direct impact. In a specific embodiment, the chamber and/or impact capsules may be capable of withstanding a crushing impact three times greater than the impact causing a grade 3 concussion.

The concussion indicator may be attached to any helmet. Examples of helmets may include sports helmets such as baseball, football, hockey or lacrosse, recreational helmets such as boating, skiing, motorcycle or bicycle helmets, construction helmets and the like.

Further, the concussion indicator may be attached to an inside or outside of the helmet. In many situations, a placement of the indicator on the outside of a helmet may be desirable because often times those with concussions do not appreciate the severity of their situations. This causes many to try to "tough it out." With the indicator on the outside, observers may see the indicator and determine the potential for concussion without the injured party having to be involved.

Figure 1:
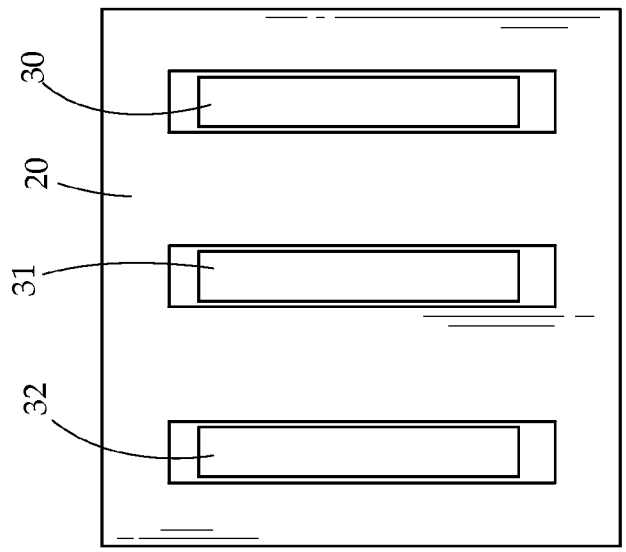
FIG. 1 provides a front view of an embodiment of the concussion indicator.

Turning now to FIG. 1, a front view of an embodiment of the concussion indicator is provided. The concussion indicator is formed from a base 10 that provides the structure for the concussion indicator. Three chambers 11, 12, and 13 are formed into the base 10. The chambers 11, 12, 13 are isolated from each other by two walls, however in other embodiments; a single wall may separate the chambers. In this particular embodiment, the chambers 11, 12, 13, have a substantially trapezoidal shaped cross section. The chambers 11, 12, 13, have a hollow interior portion wherein an impact capsule (not shown) may be secured. Further, in other embodiments, the chambers may not be separated as is shown in the figures.

Markings 14 are disposed on a front of each chamber 11, 12, 13. These markings 14 indicate three different grades of concussion. An opening 15 is formed by each chamber 11, 12, 13 at the front. The openings 15 allow an observer to see if an impact capsule (not shown) has triggered, causing a change in color and indicating the likelihood of a concussion for the helmet wearer.

Figure 2:
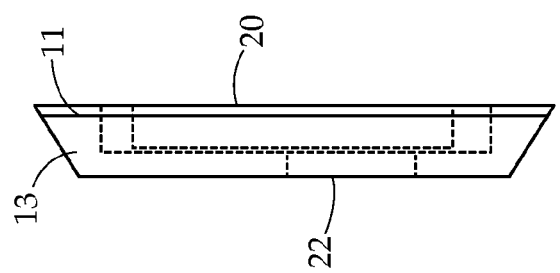
FIG. 2 provides a side view of an embodiment of the concussion indicator

FIG. 2 provides a side view of an embodiment of the concussion indicator. A rear face 20 of the base 10 can be seen. A front wall 22 of chamber 13 defines a front of the concussion indicator.

FIG. 3 provides a rear cut away view of an embodiment of the concussion indicator. A rear 20 of the base 10 can be seen. An interior of chambers 11, 12 and 13 is exposed, showing impact capsules 30, 31 and 32. The impact capsules 30, 31, 32 are secured within each chamber, and are configured to visually indicate when they are accelerated at a rate likely to cause a concussion. Capsule 30 may be configured to indicate a likelihood of a grade 1 concussion. Capsule 31 may be configured to indicate a likelihood of a grade 2 concussion. Capsule 32 may be configured to indicate a likelihood of a grade 3 concussion.

Figure 4:
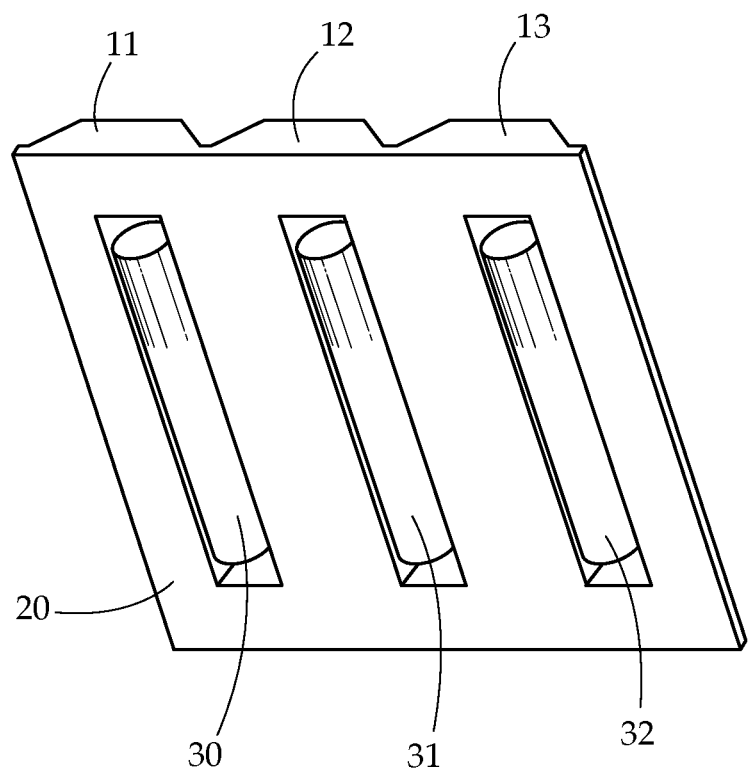
FIG. 4 provides a perspective view of an embodiment of the concussion indicator

FIG. 4 provides a perspective view of the concussion indicator. The rear surface 20 and impact capsules 30, 31, 32 can be seen in the chambers 11, 12, 13. In this view, the impact capsules 30, 31, 32 are removable from a rear of the base 10. The capsules may be held in position by, for example, a pressure fitting, snap fitting, or the like. In some embodiments, these impact capsules may be replaceable. In other embodiments, the rear may be fully or partially removable, and the impact capsules may be covered by the rear 20 of the base 10.

Figure 5:
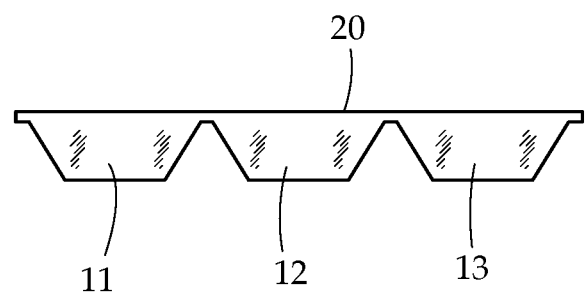
FIG. 5 provides a top view of an embodiment of the concussion indicator

FIG. 5. provides a top view of an embodiment of the concussion indicator. In this embodiment, a substantially trapezoidal cross sectional shape of each chamber 11, 12, 13 can be seen. The rear 20 of the base 10 is configured for attachment to the helmet (not shown).

While several variations of the present invention have been illustrated by way of example in preferred or particular embodiments, it is apparent that further embodiments could be developed within the spirit and scope of the present invention, or the inventive concept thereof. However, it is to be expressly understood that such modifications and adaptations are within the spirit and scope of the present invention, and are inclusive, but not limited to the following appended claims as set forth.

What is claimed is:

1. A concussion indicator comprising:
   a base;
   a first impact capsule attached to the base, configured to provide a visual indication upon receiving an impact causing acceleration at a rate likely to cause a grade one concussion;
   a second impact capsule attached to the base, configured to provide a visual indication upon receiving an impact causing an acceleration at a rate likely to cause a grade two concussion;
   a third impact capsule attached to the base, and configured to provide visual indication upon receiving an impact causing an acceleration at a rate likely to cause a grade three concussion;
   wherein the impact capsules are arranged in ascending indicating order, the first impact capsule being adjacent to the second impact capsule, the third impact capsule being adjacent to the second impact capsule.

2. The concussion indicator of claim 1 wherein the first, second, and third impact capsules are removable from the base.

3. The concussion indicator of claim 2 wherein the rear of the base defines a first opening allowing the first impact capsule to be removed from the base.

4. The concussion indicator of claim 2 wherein the first, second, and third impact capsules are removable from the base through the rear of the base.

5. The concussion indicator of claim 1 wherein the base further comprises a first wall between a first chamber of the base and a second chamber of the base, and a second wall between the second chamber and a third chamber of the base, the first impact capsule being positioned in the first chamber, the second impact capsule being positioned in the second chamber, the third impact capsule being positioned in the third chamber.

6. The concussion indicator of claim 1 wherein the base has a substantially rectangular rear face.

7. The concussion indicator of claim 1 wherein an outer face of the base adjacent to the first impact capsule comprises a first marking to indicate a grade one concussion;
   wherein an outer face of the base adjacent to the second impact capsule comprises a second marking to indicate a grade two concussion; and
   wherein an outer face of the base adjacent to the third impact capsule comprises a third marking to indicate a grade three concussion.

8. A helmet having the concussion indicator of claim 1, wherein the concussion indicator is attached to an outer surface of the helmet by an adhesive disposed on the rear of the base.

9. A helmet having the concussion indicator of claim 1, wherein the concussion indicator is attached to an inner surface of the helmet by an adhesive disposed on the rear of the base.

10. The concussion indicator of claim 1 wherein each of the first, second and third impact capsules comprises a substantially transparent cylinder, and a membrane within the cylinder separating two compounds, the membrane having a different material composition from the cylinder, the two compounds configured to cause a visible change in color when mixed, the membrane configured to rupture upon a predetermined acceleration.

11. The concussion indicator of claim 1 wherein each impact capsule is crush resistant and capable of withstanding a direct impact approximately three times greater than the impact causing an acceleration at a rate likely to cause a grade three concussion.

12. The concussion indicator of claim 1 wherein the base defines a window allowing viewing of at least one of the first impact capsule, second impact capsule, and third impact capsule from a front of the base.

13. A concussion indicator comprising:
   a base;
   a first impact capsule attached to the base, configured to provide a visual indication upon receiving an impact causing acceleration at a rate likely to cause a concussion;
   a second impact capsule attached to the base, configured to provide a visual indication upon receiving an impact causing an acceleration at a rate likely to cause a severe concussion;
   wherein the impact capsules are arranged in ascending indicating order, the second impact capsule being to the right of, and adjacent to, the second impact capsule.

14. The concussion indicator of claim 13 wherein the first, and second impact capsules are removable from the base.

15. The concussion indicator of claim 14 wherein the first and second impact capsules are removable from the base through the rear of the base.

16. The concussion indicator of claim 13 wherein the base further comprises a first wall between a first chamber of the base and a second chamber of the base, the first impact capsule being positioned in the first chamber, the second impact capsule being positioned in the second chamber.

17. The concussion indicator of claim 13 wherein an outer face of the base adjacent to the first impact capsule comprises a marking to indicate a grade one concussion;
 wherein an outer face of the base adjacent to the second impact capsule comprises a marking to indicate a grade two concussion.

18. A helmet having the concussion indicator of claim 13, wherein the concussion indicator is attached to an outer surface of the helmet by the adhesive disposed on the rear of the base.

19. The concussion indicator of claim 13 wherein each of the first and second impact capsules comprises a substantially transparent cylinder, and a membrane within the cylinder separating two compounds, the membrane having a different material composition from the cylinder, the two compounds configured to cause a visible change in color when mixed, the membrane configured to rupture upon a predetermined acceleration.

20. The concussion indicator of claim 13 wherein each impact capsule is crush resistant and capable of withstanding a direct impact approximately three times greater than the impact causing an acceleration at a rate likely to cause a grade three concussion.

* * * * *